United States Patent
Sauer et al.

(10) Patent No.: US 10,744,062 B2
(45) Date of Patent: Aug. 18, 2020

(54) COMPRESSIBLE AND RESILIENT SEXUAL AID DEVICE

(71) Applicant: Emily Sauer LLC, Brooklyn, NY (US)

(72) Inventors: Emily Sauer, Brooklyn, NY (US); Andrew Scott Brase, Brooklyn, NY (US)

(73) Assignee: Emily Sauer LLC, Brooklyn, NY (US)

( * ) Notice: Subject to any disclaimer, the term of this patent is extended or adjusted under 35 U.S.C. 154(b) by 228 days.

(21) Appl. No.: 15/876,733

(22) Filed: Jan. 22, 2018

(65) Prior Publication Data
US 2019/0224069 A1     Jul. 25, 2019

(51) Int. Cl.
*A61F 5/41* (2006.01)
*A61H 19/00* (2006.01)

(52) U.S. Cl.
CPC .............. *A61H 19/50* (2013.01); *A61H 19/34* (2013.01); *A61H 19/32* (2013.01)

(58) Field of Classification Search
CPC .............................. A61F 5/41; A61F 2005/414
USPC ...................................................... 600/38–41
See application file for complete search history.

(56) References Cited

U.S. PATENT DOCUMENTS

| | | | | |
|---|---|---|---|---|
| 4,224,933 A * | 9/1980 | Reiling | ...................... | A61F 5/41 600/39 |
| 4,252,305 A * | 2/1981 | Pasch | .................... | B25B 1/2452 269/274 |
| 5,370,131 A * | 12/1994 | Hess | .......................... | A61F 6/04 128/842 |
| 5,695,444 A * | 12/1997 | Chaney | ..................... | A61F 5/41 600/38 |
| 5,836,864 A * | 11/1998 | Clark, Jr. | .................. | A61F 5/41 600/38 |
| 6,251,067 B1 | 6/2001 | Strickholm | | |
| 6,319,194 B1 * | 11/2001 | Wulf | ......................... | A61F 5/41 600/41 |
| 2003/0199734 A1 * | 10/2003 | Anderson | ................. | A61F 5/41 600/38 |
| 2009/0234182 A1 | 9/2009 | Buchholtz | | |

FOREIGN PATENT DOCUMENTS

| | | |
|---|---|---|
| DE | 554178 A | 7/1932 |
| FR | 3005849 B1 | 4/2016 |
| KR | 20110005083 U | 5/2011 |
| KR | 101516523 B1 | 4/2015 |
| WO | 2017188649 A1 | 11/2017 |

* cited by examiner

*Primary Examiner* — Samuel G Gilbert
(74) *Attorney, Agent, or Firm* — Stoyanov Law PLLC; Roy L. Chan (57) ABSTRACT

A compressible and resilient sexual aid device has a module. The module has a rim, a neck, a base, and an aperture. The neck has a first end and a second end. The rim is connected to the first end. The base is connected to the second end. The aperture extends from the rim through the neck and through the base. The rim has a first diameter. The neck has a second diameter. The base has a third diameter. The first diameter is greater than the second diameter. The third diameter is greater than the first diameter and the second diameter. The module is compressible and resilient. Additional modules may be added to the device according to a user's preference.

9 Claims, 6 Drawing Sheets

COMPRESSIBLE AND RESILIENT SEXUAL AID DEVICE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention is related to a compressible and resilient sexual aid device that provides impact cushioning, customizable depth penetration and friction reduction during sexual intercourse and penetration, and can also secure and position additional sexual aids, including condoms, rings, sleeves, prostheses, vibrators, etc.

Some individuals may desire to limit the depth of penetration during intercourse for various reasons. In one example, restriction penetration may reduce unwanted pain and therefore extend the duration of stimulating intercourse. In another example, intercourse involving a long penis or lack of female arousal, may result in collision dyspareunia, where unpleasant pain results from the penis colliding with the cervix. In another example, some individuals may experience pelvic pain during sexual penetration due to one or a combination of the diagnoses and symptoms that fall under the Genito-Pelvic Pain/Penetration Disorder (GPPPD) including dyspareunia (pain before, during, or after penetrative intercourse) and vaginismus (involuntary tightening of the pelvic floor muscles). Causes of dyspareunia may include endometriosis, ovarian cysts, uterine fibroids, pelvic floor muscle or ligament tension, adhesions, scar tissue, anatomical mismatching (retroverted uterus, length of the male appendage, depth/length of orifice), insufficient arousal to facilitate vaginal tenting, pre and postnatal/postmenopausal hormone changes, postnatal prolapse, and Post Traumatic Stress Disorder (PTSD)/neurological related factors that contribute to pain retention.

Some individuals may also desire to cushion or slow the last stage of penetration for various reasons, including to reduce discomfort or pain against the vulva or pubic region.

The present invention helps limit the depth of penetration during intercourse, helps cushion the penetration, and can help reduce or solve these and other problems associated with discomfort or pain during sexual intercourse and penetration.

For some individuals, maintaining sexual aids on a penis may be problematic or uncomfortable for a variety of reasons. For example, a condom, sleeve, or external prosthesis may easily slip off due to lubrication, size mismatch between the sexual aid and the penis, among other reasons. In another example, an external penile prosthesis may require multiple uncomfortable straps to maintain in place on the penis. The present invention helps secure sexual aids on the penis and help reduce or solve these and other problems.

BRIEF SUMMARY OF THE INVENTION

An object of the present invention is a compressible and resilient sexual aid device comprising a module. The module comprises a rim, a neck, a base, and an aperture. The neck comprises a first end and a second end. The rim is connected to the first end. The base is connected to the second end. The aperture extends from the rim through the neck and through the base. The rim has a first diameter. The neck has a second diameter. The first diameter is greater than the second diameter. The module is compressible and resilient.

In another object of the present invention, the base has a third diameter. The third diameter is greater than the first diameter and the second diameter.

In another object of the present invention, the module is made of one of silicone, body safe silicone, or rubber blend.

In yet another object of the present invention, the compressible and resilient sexual aid device further comprises at least one additional module. Each of the at least one additional module comprises an additional rim, an additional neck, an additional base, and an additional aperture. The additional neck comprises an additional first end and an additional second end. The additional rim is connected to the additional first end. The additional base is connected to the additional second end. The additional aperture extends from the additional rim through the additional neck to the additional base. The additional rim has an additional first diameter. The additional neck has an additional second diameter. The additional first diameter is greater than the additional second diameter. Each of the at least one additional module is compressible and resilient. The rim is coupled to the additional base.

In another object of the present invention, the additional base has an additional third diameter. The additional third diameter is greater than the additional first diameter and the additional second diameter.

In another object of the present invention, each of the at least one additional module is made of one of silicone, body safe silicone, or rubber blend.

BRIEF DESCRIPTION OF THE SEVERAL VIEWS OF THE DRAWING

The advantages and features of the present invention will be better understood as the following description is read in conjunction with the accompanying drawings, wherein.

DETAILED DESCRIPTION OF THE INVENTION

As illustrated in the figures, embodiments of a compressible and resilient sexual aid device 100 comprises a module 110. The module 110 comprises a rim 111, a neck 112, a base 113, and an aperture 114. The neck 112 comprises a first end 112b and a second end 112c. The rim 111 is connected to the first end 112b. The base 113 is connected to the second end 112c. The aperture 114 extends from the rim 111 through the neck 112 to the base 113. The rim 111 has a first diameter 111a. The neck 112 has a second diameter 112a. The base 113 has a third diameter 113a. The first diameter 111a is greater than the second diameter 112a. The third diameter 113a is greater than the first diameter 111a. The module 110 is compressible and resilient.

In some embodiments, the module 110 may be made of medical grade silicone or body safe silicone. In other embodiments, module 110 may be made of a rubber blend.

Figures 4A, 4B:
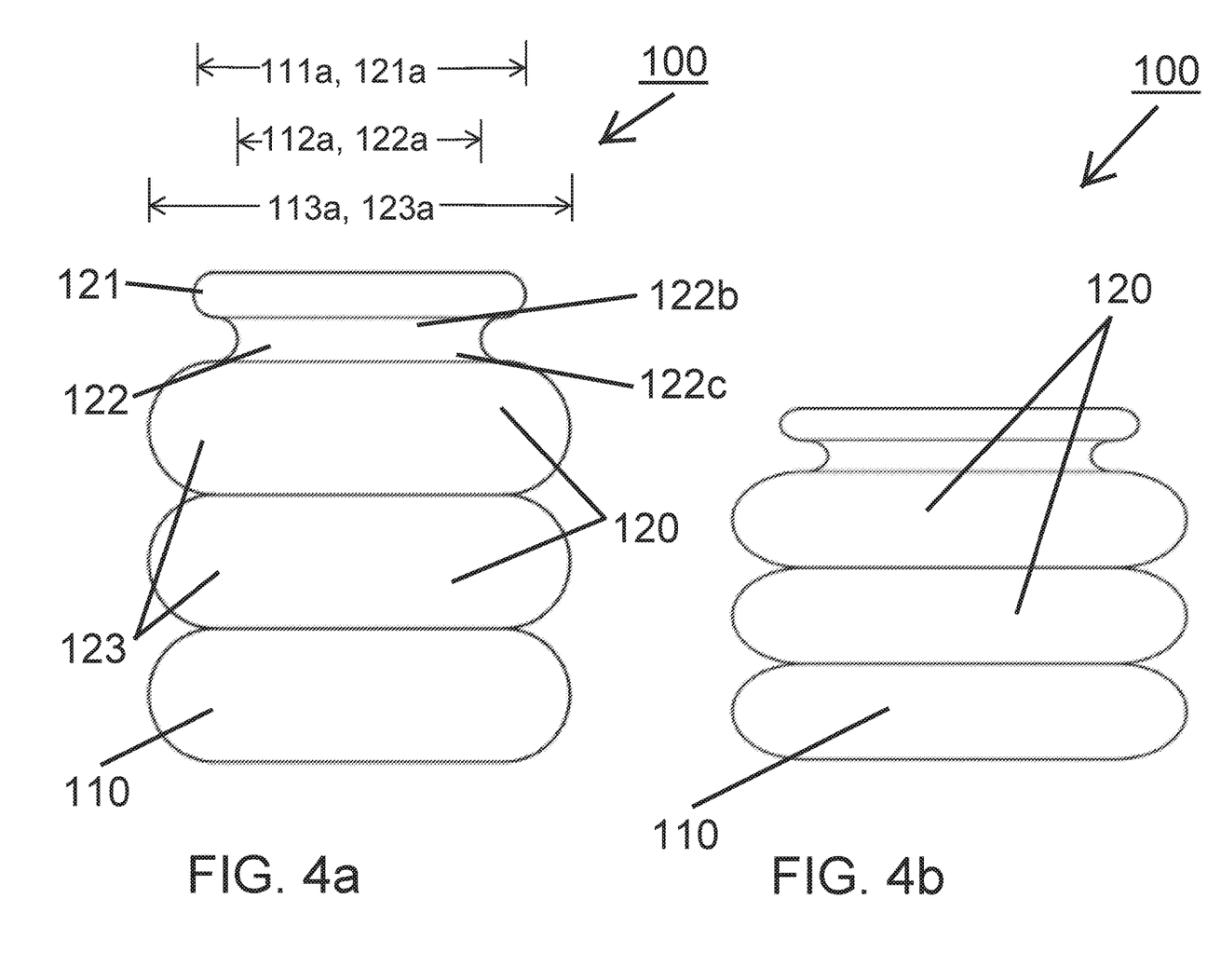
FIG. 4a-4b are side views of embodiments of the present invention.
Figure 5:
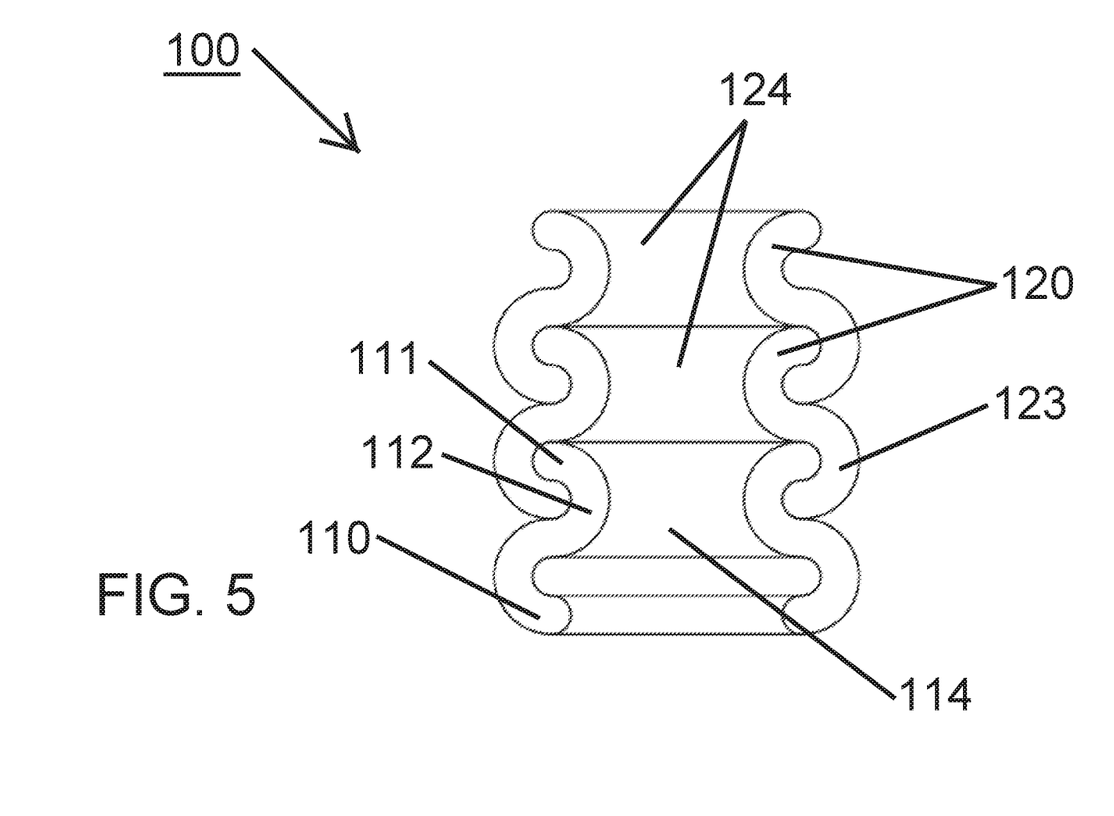
FIG. 5 is a cross sectional view of an embodiment of the present invention.

As the examples in FIGS. 4a, 4b and 5, illustrate, in other embodiments of the present invention, the compressible and resilient sexual aid device 100 may further comprise at least one additional module 120. Each of the additional modules 120 comprises an additional rim 121, an additional neck 122, an additional base 123, and an additional aperture 124. The additional neck 122 comprises an additional first end 122b and an additional second end 122c. The additional rim 121 is connected to the additional first end 122b. The additional base 123 is connected to the additional second end 122c. The additional aperture 124 extends from the additional rim 121 through the additional neck 122 to the additional base 123. The additional rim 121 has an additional first diameter 121a. The additional neck 122 has an additional second diameter 122a. The additional base 123 has an additional third diameter 123a. The additional first diameter 121a is greater than the additional second diameter 122a. The additional third diameter 123a is greater than the additional first diameter 121a. Each of the additional modules is compressible and resilient. The rim 111 of the module 110 may be coupled to the additional base 123 of an additional module 120.

In some embodiments, each of the additional modules 120 may be made of medical grade silicone or body safe silicone. In other embodiments, each of the additional modules 120 may be made of a rubber blend.

An embodiment of the compressible and resilient sexual aid device 100 comprising of only module 110 (not shown) used during intercourse slows and cushions penetration and eventually stops and limits the penetration depth as follows: as appendage 210 of a first user penetrates orifice 200 of a second user, rim 111 comes in contact with the body of the second user and compresses and deforms from the pressure between the first and second users' bodies, thereby providing initial resistance against appendage 210 and cushioning and slowing of the penetration. As the penetration continues, rim 111 further compresses and deforms and transfers the force from the first and second users' bodies through the neck 112 to the base 113 along the "S" shape of module 110. As penetration continues, the pressure between the first and second users' bodies further compresses rim 111, neck 112, and base 113, thereby further cushioning and slowing the rate of penetration. As rim 111, neck 112, and base 113 compress even further from the pressure between the first and second users' bodies, the compressible and resilient sexual aid device 100 resists the penetration, eventually stopping the penetration when the compression force is sufficiently large.

Another embodiment of the compressible and resilient sexual aid device 100 comprising one or more additional modules 120 linked to module 110, provide additional limitation to the amount of penetration and additional cushioning and slowing of penetration as the additional rim 121 comes in contact with the orifice 200 and transfers the pressure through the additional neck 122 to the base 123. Additional base 123 may transfer the force to another additional rim 121 of another additional module 120 if one is linked. Additional base 123 of an additional module 120 linked to module 110 will transfer the force to rim 111. The embodiment of the compressible and resilient sexual aid device 100 of this example provides additional limitation to the penetration and additional cushioning and slowing of the penetration.

Figure 6A:
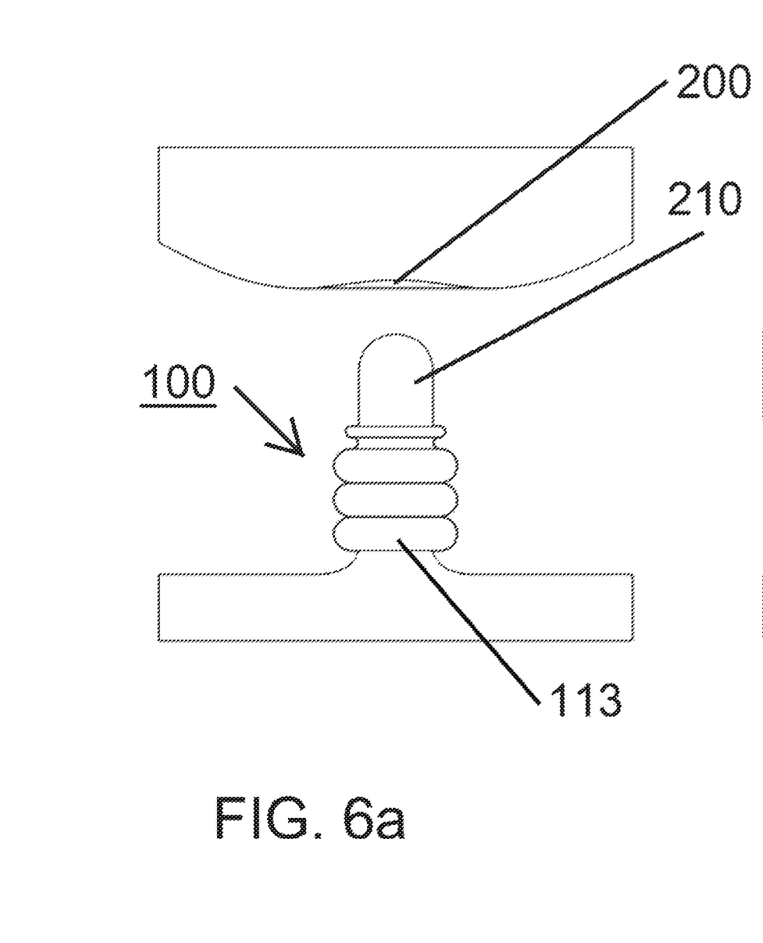
FIG. 6a-6b are side views of embodiments of the present invention.
Figure 6B:
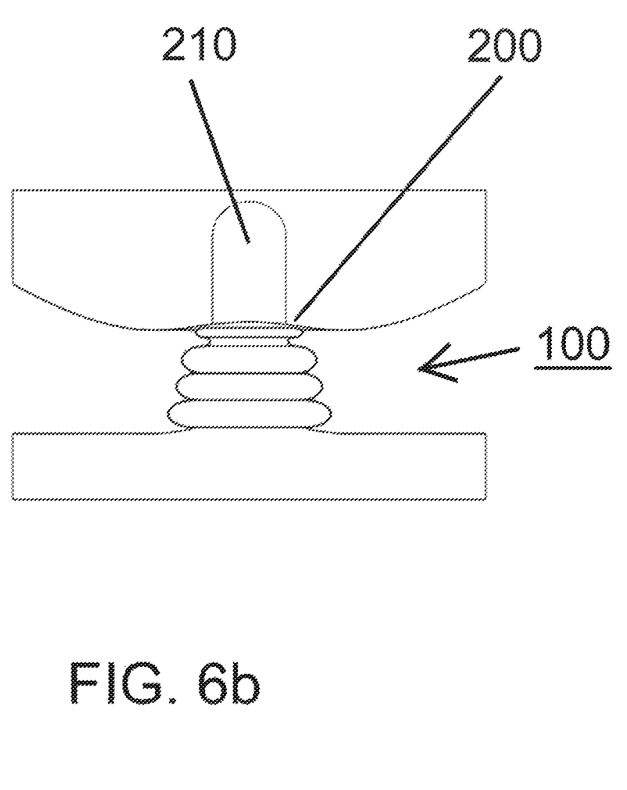

FIGS. 4a-b, 5, and 6a-b illustrate embodiments of the present invention where the module 110 is coupled to at least one additional module 120. FIG. 5 illustrates a cross section of a module 110 coupled to two additional modules 120. The module 110 and each of the additional modules 120 are configured to be removably linked or removable coupled together. By compressing or deforming the rim 111 of the module 110, the rim 111 may be inserted into the additional aperture 124 near the additional base 123 of an additional module 120, as illustrated in the embodiment of FIG. 5. As also illustrated in FIG. 5, another additional module 124 may be added and coupled to the compressible and resilient sexual aid device 100. As shown in FIG. 5, the coupled module 110 and additional modules 120 forms one continuous aperture by where the aperture 114 in communication with the additional apertures 124. As shown in FIGS. 6a-b, this allows a user to insert a penetrating appendage 210 through the aperture 114 at the base 113 through the rest of the module 110 and the additional modules 120, and out of the additional aperture 124 of the last additional module 120 at the additional rim 121. While the above figures only show two additional modules removably linked to module 110, compressible and resilient sexual aid device 100 may be customized by removably linking only one additional module 120 to module 110, or by removably linking more than two modules 120 to module 110.

Figure 1:
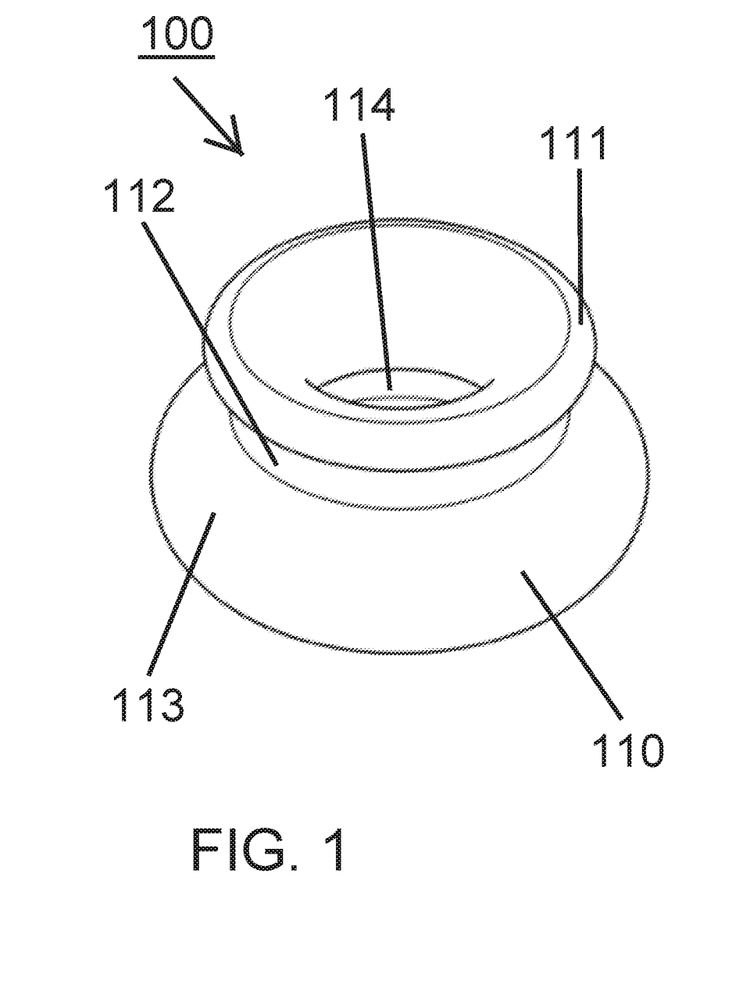
FIG. 1 is a perspective view of an embodiment of the present invention.
Figure 2:
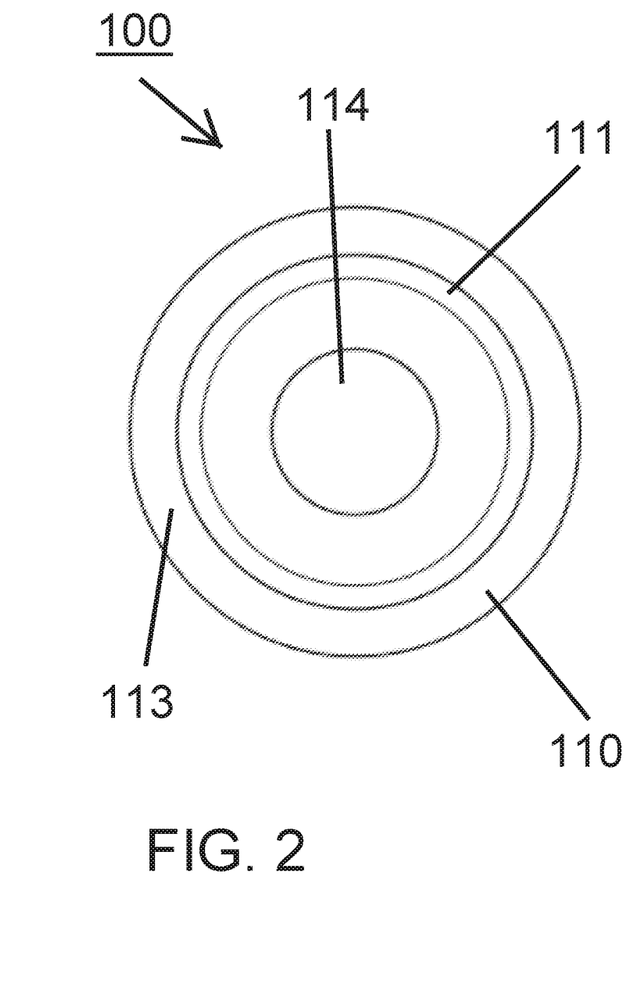
FIG. 2 is a top view of an embodiment of the present invention.
Figure 3A:
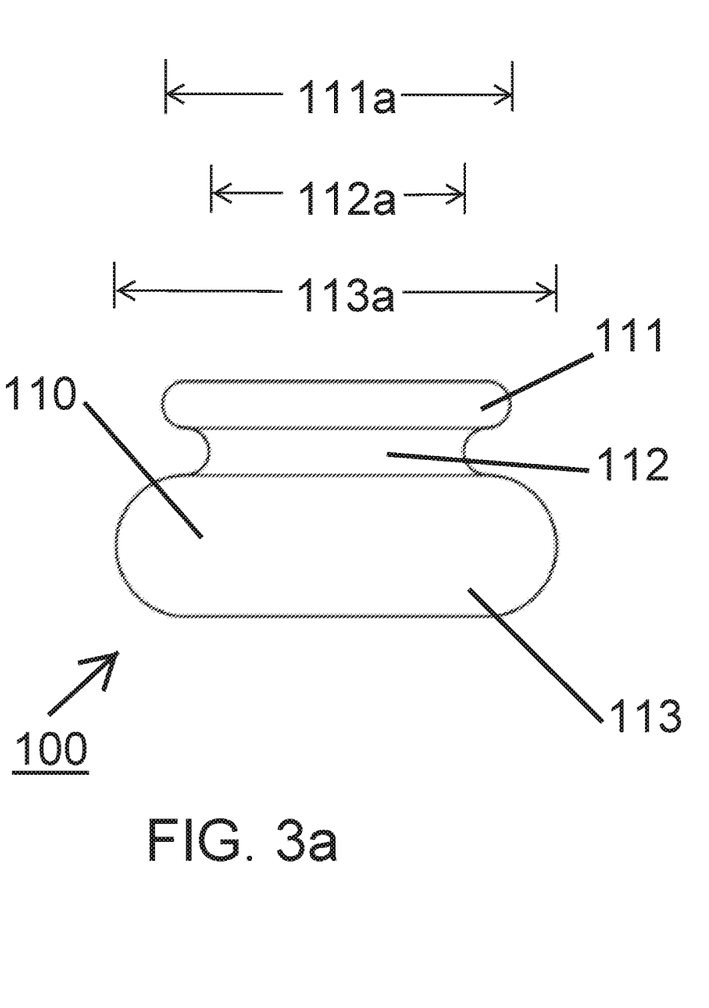
FIG. 3a-3b are side views of embodiments of the present invention.

The module 110 is configured to have different diameters for the rim 111, the neck 112 and the base 113, as shown in the figures, for example, FIG. 3a. Similarly, each additional module 120 is configured with different diameters for the additional rim 121, the additional neck 122 and the additional base 123, as shown in the figures, for example, FIG. 4a. These different diameters aid in the coupling of the module 110 to an additional module 120 and the coupling of an additional module 120 to another additional module 120. As illustrated in FIG. 5, the "S" shapes formed by the rim 111, the neck 112 and the base 113, and the additional rim 121, the additional neck 122 and the additional base 123, of the module 110 and additional modules 120, respectively, provides a linking mechanism for the rim 111 to the additional base 123 and for the additional rim 121 to another additional base 123. The figures illustrate exemplary embodiments as having an "S" shaped cross section of module 110 and additional modules 120; however, one of ordinary skill in the art understands that the module 110 and additional modules 120 may have a cross section of a different shape.

The compressible and resilient sexual aid device 100 gradually cushions impact and reduces friction during penetration. Linking additional modules 120 to the module 110 provides additional impact cushioning, customizable depth penetration and friction reduction. Although the figures illustrate embodiments with a module 110 coupled to two additional modules 120, the present invention may be practiced with as many additional modules 120 as users require. With more additional modules 120, the compressible and resilient sexual aid device 100 lengthens in size, making it customizable for each user's physiological preference.

Figure 3B:
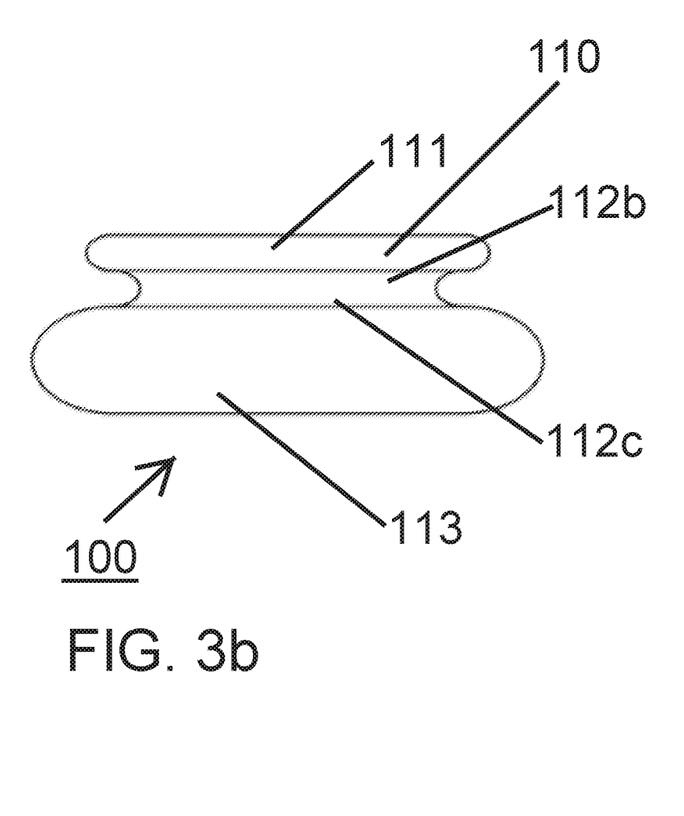

The module 110 and each of the additional modules 120 are compressible and resilient. FIG. 3a illustrates the module 110 in its natural resilient state and FIG. 3b illustrates the module 110 in its compressed state. Similarly, FIG. 4a illustrates the module 110 and the additional modules 120 in their natural resilient states and FIG. 4b illustrates the module 110 and the additional modules 120 in their compressed states. The compressible and resilient sexual aid device 100 may be wrapped around the base of a penetrating appendage 210, as illustrated in FIGS. 6a and 6b, before penetration of a receiving orifice 200. The penetrating appendage 210 may be a penis or an artificial phallus, dildo, or similar; the receiving orifice 200 may be a vagina, anus or other orifice. Upon penetration, the compressible and resilient sexual aid device 100 compresses, as shown in FIG. 6b. Upon partial or full removal, the compressible and resilient sexual aid device 100 springs back to its original resilient state, as shown in FIG. 6a.

The module 110 and the additional modules 120 are preferably made of silicone, and more preferably medical grade platinum-cure silicone. In other embodiments, the module 110 and the additional modules 120 may be made of body safe silicone, rubber blend, or similar compressible and resilient materials. In such embodiments, the compressible and resilient sexual aid device 100 may be washed and reused.

The compressible and resilient sexual aid device 100 may be used in conjunction with penile sexual aids, such as condoms, sleeves, and prostheses. A user would put on the penile sexual aid first, followed by the compressible and resilient sexual aid device 100 over the penile sexual aid. The compressible and resilient sexual aid device 100 will compress the penile sexual aid and secure it to the appendage 210, preventing slippage or dislocation.

Figure 7:
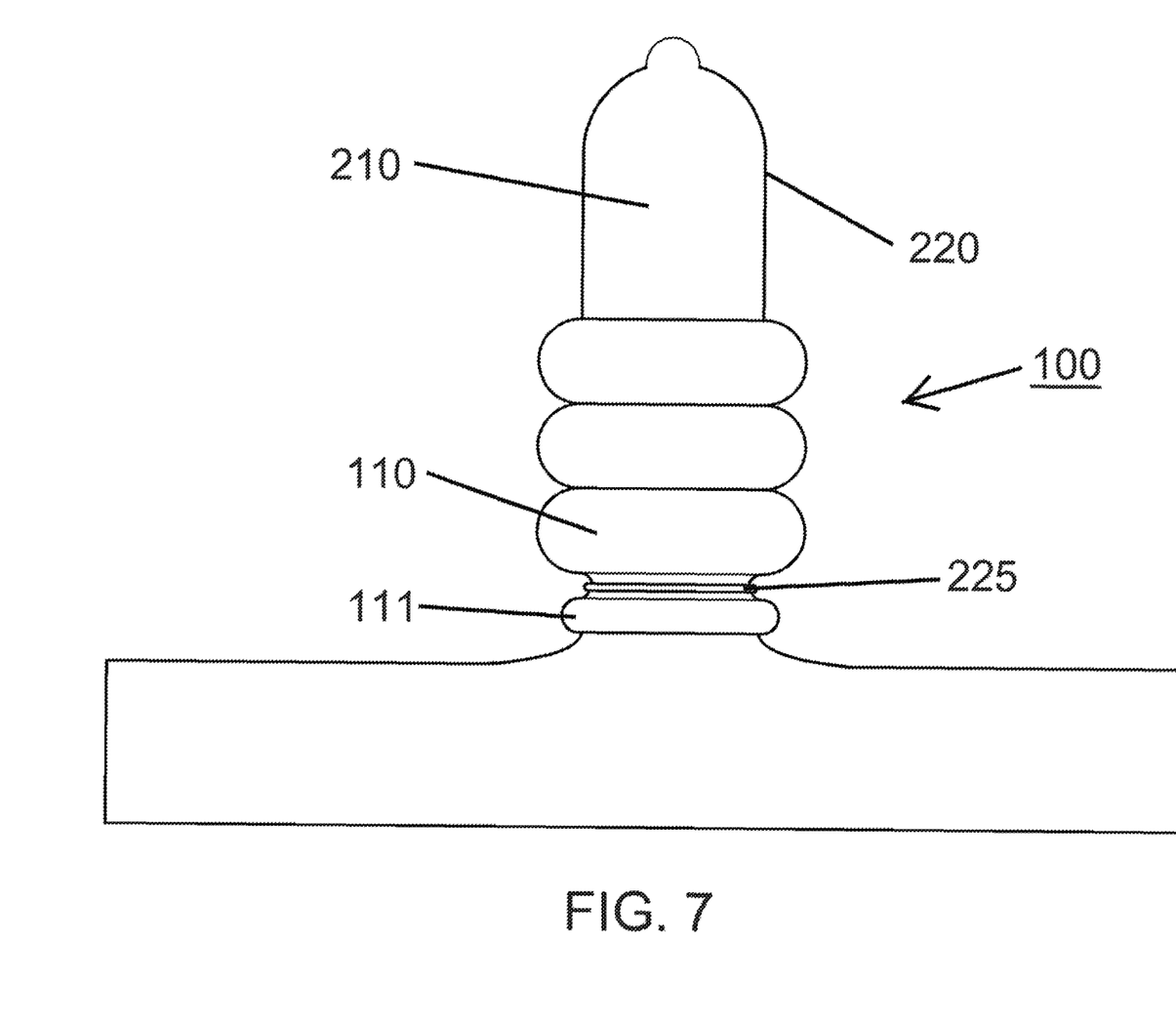
FIG. 7 is a side view of an embodiment of the present invention.

In one embodiment, when compressible and resilient sexual aid device 100 is used with a condom or similar penile sexual aid, the user can secure the penile sexual aid to the compressible and resilient sexual aid device 100 by wrapping the rolled ring of condom around the base 113 of the module 110. As illustrated in FIG. 7, a condom 220 may placed over the penetrating appendage 210. Then, the compressible and resilient sexual aid device 100 (in this example, the module 110 is removably linked to two additional modules 120). The condom end 225 may then be rolled over the rim 111 of the module 110, thereby securing the condom 220 to the compressible and resilient sexual aid device 100. Alternatively, depending upon the length of the condom 220, the length of the penetrating appendage 210, and the number of additional modules 120 utilized, the condom end 225 may be rolled over (a) the rim 111 of the module 100 (as illustrated); (b) the entire module 110 (not illustrated); (c) part of the compressible and resilient sexual aid device 100; or (d) the entire the compressible and resilient sexual aid device 100 (not illustrated). When utilized with a penile sexual aid, such as a condom as illustrated in FIG. 7, the penetrating appendage 210 may be inserted through the rim 111 of the compressible and resilient sexual aid device 100. Alternatively, the penetrating appendage 210 may be inserted through the base 113 of the compressible and resilient sexual aid device 100, as illustrated in FIG. 6a. In FIG. 7, the rim 111 is nearest the base of the penetrating appendage 210; whereas, in FIG. 6a, the base 113 is nearest the base of the penetrating appendage 210.

While the invention has been described with reference to exemplary embodiments, it will be understood by those skilled in the art that various changes, omissions, and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiments disclosed as the best mode contemplated for carrying out this invention, but that the invention will include all embodiments falling within the scope of the appended claims. Moreover, unless specifically stated any use of the terms first, second, additional, etc. do not denote any order or importance, but rather the terms first, second, additional, etc. are used to distinguish one element from another.

We claim:

1. A compressible and resilient sexual aid device comprising:
   a module, wherein the module comprises:
   a rim,
   a neck, wherein the neck comprises:
      a first end, and
      a second end;
   a base, and
   an aperture;
   wherein the rim is connected to the first end;
   wherein the base is connected to the second end;
   wherein the aperture extends from the rim through the neck and through the base;
   wherein the rim has a first diameter;
   wherein the neck has a second diameter;
   wherein the first diameter is greater than the second diameter;
   wherein the neck is compressible and resilient
   wherein the neck is in a compressed form when a longitudinal compression force is applied between the rim and the base;
   wherein in the compressed form, the neck resists, absorbs and cushions the longitudinal compression force; and,
   wherein the neck returns to an uncompressed form when the longitudinal compression force is removed.

2. The compressible and resilient sexual aid device of claim 1, wherein the base has a third diameter;
   wherein the third diameter is greater than the first diameter; and,
   wherein the third diameter is greater than the second diameter.

3. The compressible and resilient sexual aid device of claim 1, wherein the module is made of one of silicone, body safe silicone, or rubber blend.

4. The compressible and resilient sexual aid device of claim 1, wherein a cross section of the module is a curve substantially in the shape of an S-letter.

5. A compressible and resilient sexual aid device comprising:
   a first module, wherein the first module comprises:
   a first rim,
   a first neck,
   a first base, and
   a first aperture;
   wherein the first rim is connected to the first neck;
   wherein the first base is connected to the first neck;
   wherein the first aperture extends from the first rim through the first neck through the first base;
   wherein the first rim has a first rim diameter;
   wherein the first neck has a first neck diameter;
   wherein the additional first rim diameter is greater than the first neck diameter; and
   wherein the first neck is compressible and resilient; and, a second module, wherein the second module comprises:
a second rim,
a second neck;
a second base, and
a second aperture;
wherein the second rim is connected to the second neck:
wherein the second base is connected to the second neck;
wherein the second aperture extends from the second rim through the second neck through the second base;
wherein the second rim has a second rim diameter:
wherein the second neck has a second neck diameter:
wherein the second rim diameter is greater than the second neck diameter; and;
wherein the neck is compressible and resilient; and,
wherein the first rim is coupled to the second base;
wherein the first neck and the second neck are in a compressed form when a longitudinal compression force is applied between the first base and the second rim;
wherein in the compressed form, the first neck and the second neck resist, absorb and cushion the longitudinal compression force; and,
wherein the first neck and the second neck return to an uncompressed form when the longitudinal compression force is removed.

6. The compressible and resilient sexual aid device of claim 5, wherein the first base has a first base diameter;
wherein the first base diameter is greater than the first rim diameter;
wherein the first base diameter is greater than the first neck diameter;
wherein the second base has second base diameter;
wherein the second base diameter is greater than the second rim diameter; and,
wherein the second base diameter is greater than the second neck diameter.

7. The compressible and resilient sexual aid device of claim 5, wherein the first module and second module are made of one of silicone, body safe silicone, or rubber blend.

8. The compressible and resilient sexual aid device of claim 5, wherein the first rim is coupled to the second base by inserting a portion of the first rim in the second base.

9. The compressible and resilient sexual aid device of claim 5, wherein a cross section of the first module is a curve substantially in the shape of an S-letter, and wherein a cross section of the second module is a curve substantially in the shape of an S-letter.

* * * * *